(12) United States Patent
Goldsmith et al.

(10) Patent No.: US 9,757,281 B2
(45) Date of Patent: Sep. 12, 2017

(54) EXTRA-PROTECTION PADS AND RELATED METHODS

(71) Applicants: Lorrie Goldsmith, Manlius, NY (US); David Goldsmith, Manlius, NY (US); Gary Shuster, Fresno, CA (US)

(72) Inventors: Lorrie Goldsmith, Manlius, NY (US); David Goldsmith, Manlius, NY (US); Gary Shuster, Fresno, CA (US)

( * ) Notice: Subject to any disclaimer, the term of this patent is extended or adjusted under 35 U.S.C. 154(b) by 75 days.

(21) Appl. No.: 14/578,186

(22) Filed: Dec. 19, 2014

(65) Prior Publication Data

US 2015/0173969 A1    Jun. 25, 2015

Related U.S. Application Data

(60) Provisional application No. 61/919,375, filed on Dec. 20, 2013.

(51) Int. Cl.
*A61F 13/472* (2006.01)
*A61F 13/15* (2006.01)
*A61F 13/475* (2006.01)

(52) U.S. Cl.
CPC ...... *A61F 13/15747* (2013.01); *A61F 13/475* (2013.01); *A61F 13/4758* (2013.01); *A61F 13/47218* (2013.01); *A61F 13/47227* (2013.01); *A61F 13/47272* (2013.01); *Y10T 156/1051* (2015.01)

(58) Field of Classification Search
CPC .............. A61F 13/472; A61F 13/47209; A61F 13/47218; A61F 13/47227; A61F 13/47272; A61F 13/474; A61F 13/4758; A61F 13/505; A61F 2013/4729
See application file for complete search history.

(56) References Cited

U.S. PATENT DOCUMENTS

| 3,367,334 | A | * | 2/1968 | Testa | A61F 13/474 |
| | | | | | 604/370 |
| 5,704,932 | A | * | 1/1998 | Hibbard | A61F 13/474 |
| | | | | | 604/385.01 |
| 5,720,738 | A | * | 2/1998 | Clark | A61F 13/474 |
| | | | | | 604/385.01 |
| H1788 | H | * | 2/1999 | Christon | A61F 13/55145 |
| | | | | | 604/385.101 |

(Continued)

*Primary Examiner* — Lynne Anderson
(74) *Attorney, Agent, or Firm* — Sherrie M. Flynn; Coleman & Horowitt, LLP

(57) ABSTRACT

Extra-protection fins and pads, and methods of making and using extra-protection fins and pads are disclosed. The extra-protection fins and pads of the present invention comprise a first triangular face, a second triangular face attached and/or connected to the first triangular face at an angle thereby forming a front apex and a top apex, wherein the fins are configured such that the front apex catches and/or absorbs the menstrual and/or other vaginal fluids first, and the extra-protection fin fills backwards toward the top apex, thus preventing unwanted, embarrassing and annoying leakage onto clothing or bedding during periods of heavy flow and/or when lying down. The extra-protection fin may also comprise a third triangular face attached and/or connected to the first and second triangular faces, wherein a vertex of the third triangular face contacts and/or is connected to the first and second triangular faces at the top apex.

21 Claims, 8 Drawing Sheets

(56) References Cited

U.S. PATENT DOCUMENTS

| | | | | |
|---|---|---|---|---|
| 5,910,137 A * | 6/1999 | Clark | ............... | A61F 13/505 604/385.04 |
| 6,013,064 A * | 1/2000 | Yamada | ............ | A61F 13/474 604/385.01 |
| 6,652,503 B1 * | 11/2003 | Bradley | ........... | A61F 13/47272 604/385.01 |
| 6,730,067 B1 * | 5/2004 | Nukina | ............ | A61F 13/474 604/378 |
| 7,530,973 B2 * | 5/2009 | Tanio | ............ | A61F 13/4702 604/380 |
| 8,961,486 B2 * | 2/2015 | Stewart | ............ | A61F 13/47218 604/385.17 |
| 2008/0312630 A1 * | 12/2008 | Seo | ............... | A61F 13/4758 604/385.03 |
| 2010/0262098 A1 * | 10/2010 | Brusk | .............. | A61L 15/20 604/359 |

* cited by examiner

EXTRA – PROTECTION PAD LOCATED INSIDE OF PANTY

EXTRA-PROTECTION PADS AND RELATED METHODS

CROSS-REFERENCE TO RELATED APPLICATIONS

This application claims the benefit of U.S. Provisional Application No. 61/919,375 filed Dec. 20, 2013.

FIELD OF THE INVENTION

The present invention generally relates to the field of feminine hygiene products. More specifically, embodiments of the present invention pertain to disposable fins and pads which provide extra protection against leaking of menstrual fluid and/or other vaginal discharge from or around the fin or pad.

DISCUSSION OF THE BACKGROUND

Throughout history, women have used some form of menstrual protection. Early forms of menstrual pads were cloth and reusable. Disposable menstrual pads or feminine napkins became commercially available in the late 1800's or early 1900's, and are now used throughout the industrialized world. A variety of types of menstrual pads are available today, including panty liners for light flow, ultra-thin pads, which are compact yet absorbent, regular pads with mid-range absorbency, super or maxi-pads, which are designed for heavier flows, and overnight pads, which are intended to provide additional protection when used overnight and/or when lying down.

Pads made for heavier flows, and particularly pads made for overnight use, all suffer from the same deficiency—they leak, which may cause embarrassment as well as staining of clothing and/or bedding. Indeed, during periods of heavy flow, even the common alternative for pads—the tampon—can become saturated and leak. As a result, clothing and bedding may need to be laundered more frequently, costing the consumer unnecessary time and money. Washing more frequently also increases energy and water use, thereby wasting precious natural resources. When stains cannot be removed, otherwise usable clothes and/or bedding must be thrown away. This premature disposal of clothing and bedding increases cost to the consumer and waste to landfills. Beyond the financial cost, leakage may result in physical discomfort, interrupted sleep, and other negative physiological impacts.

Current solutions for overcoming leaking pads include increasing the length and/or thickness of the pad, using, at the time of manufacture, super-absorbent material in the pad, and/or using a tampon in addition to a pad. These solutions are an improvement over "regular" pads in that leaks may not occur as quickly. However, the currently available heavy flow pads do not satisfactorily correct the problem, and leaks still occur, especially at night. Using a tampon in addition to a pad may prevent leaking, but is also problematic, particularly in women who have had pelvic floor damage and cannot wear or comfortably wear a tampon. Further, women are advised not to wear a tampon to bed at night due to the risk of toxic shock syndrome. It should also be understood that leakage may occur without saturation, such as when the pad does not properly or fully conform to the physical contours of the woman.

Control of other fluids, such as urine in the case of urinary incontinence, may also fall short of full control for similar reasons.

Therefore, it is desirable to provide a disposable menstrual extra-protection fin and/or pad that prevents leakage of menstrual fluid, other vaginal discharge and/or urine during periods of heavy flow, such as at night and/or when lying down.

SUMMARY OF THE INVENTION

The present invention advantageously provides extra-protection fins and pads that prevents annoying, embarrassing and unwanted leakage of menstrual fluid, other vaginal discharge and/or urine onto clothing and/or bedding during periods of heavy flow and/or when lying down, such as at night and/or when sleeping. Embodiments of the present invention utilize an appendage (a fin), which may be triangularly-shaped and/or contoured, and may be attached to a currently available menstrual pad after purchase, or may be manufactured as part of the pad prior to purchase. The fin is configured such that the menstrual flow and/or vaginal discharge are captured first at a front apex and, as the flow continues, the fin fills backwards toward a top apex. In some embodiments of the invention, the extra-protection pad may comprise "wings" and/or an adhesive applied to the underneath of the pad, to securely attach the pad to an undergarment.

In an embodiment of the present invention, the extra-protection fin may comprise one or more malleable and/or pliable materials such as foam, "memory foam" and/or heat-sensitive thermoplastic polymers that may mold and/or conform to the contours of a person's body when in use and/or when heated. Such malleable/pliable fin may act as a "stopper," preventing the leakage of menstrual fluids, other vaginal discharge and/or urine.

In another embodiment of the present invention, the extra-protection pad comprises a coagulant and/or a topical hemostatic agent such that the menstrual fluid and/or other vaginal discharge thickens into a soft and/or semisolid mass, thereby preventing the menstrual fluid and/or other discharge from escaping and/or leaking from the pad. In other embodiments, the extra-protection pad may comprise thin layers stacked or "sandwiched" together utilizing adhesive backings, such that one or more layers, after becoming soiled, may be removed and disposed of, thereby providing a clean and sanitary surface without the need to dispose of the entire pad.

In yet another embodiment of the present invention, the pad may comprise a lip, which acts as a physical barrier to advantageously prevent leakage at or near the edges of the pad. In further embodiments, an ultra-absorbent coating agent may be sprayed onto undergarments to prevent menstrual fluid and/or other vaginal discharge from combining with the fabric. In such embodiments, the spray-on coating may be peeled off after use. In further embodiments, the coating agent may be non-absorbent, and/or may have a non-absorbent inner layer, so that the coated fabric is protected from flow and/or the flow is redirected.

Embodiments of the present invention also provide methods of making and using extra-protection fins and pads. In some embodiments, the method of making may comprise (a) forming a first triangular face and a second triangular face, (b) attaching and/or folding at an angle the first triangular face to the second triangular face at a first edge such that the first and second triangular faces form a front apex and a top apex, wherein the extra-protection fin is configured such that when the fin is positioned with the front apex at or near a woman's vagina discharging menstrual and/or other vaginal fluids and the top apex at or near the woman's anus, the front apex catches and/or absorbs the fluids first, and the extra-protection fin fills backwards toward the top apex.

In some embodiments, the method of making an extra-protection pad also comprises (c) forming a third triangular face, attaching and/or folding an angle the third triangular face to the first triangular face at a second edge and to the second triangular face at a third edge, such that a vertex of the third triangular face contacts and/or is connected to the first and second triangular faces at the top apex.

Embodiments of the present invention also provide methods of using an extra-protection fin by placing the extra-protection fin on a conventional menstrual pad such that when the menstrual pad is placed next to the body, the front apex is located at or near the vagina and the top apex is located at or near the anus, and attaching the fin to the conventional pad (e.g., by pinning, stapling, gluing, adhering, stitching, sewing). In some embodiments, attaching the extra-protection fin to the conventional pad may include grasping a protective strip positioned on a base of the fin, peeling off from the base a protective strip to expose an adhesive, and pressing the fin onto the menstrual pad.

In embodiments where the extra-protection fin is attached to a menstrual pad prior to distribution, the method of using the extra-protection pad may also comprise placing the extra-protection pad in an undergarment such that when the undergarment is worn, the extra-protection pad is adjacent to the body, the front apex of the extra-protection fin is located at or near the vagina, and the top apex of the fin is located at or near the anus, and wearing the undergarment.

Thus, embodiments of the present invention advantageously provides extra-protection fins and pads that prevent embarrassing and unwanted leakage of menstrual fluid and/or other vaginal discharge onto clothing and/or bedding during periods of heavy flow and/or when lying down, such as at night and/or when sleeping, and also advantageously provide methods of making and using extra-protection fins and pads to prevent the unwanted leakage of menstrual fluid and/or other vaginal discharge.

A more complete understanding of the extra-protection fins and pads will be afforded to those skilled in the art, as well as a realization of additional advantages and objects thereof, by consideration of the following detailed description of preferred embodiments. Reference will be made to the appended sheets of drawings, which will first be described briefly.

DETAILED DESCRIPTION OF THE PREFERRED EMBODIMENTS

Reference will now be made in detail to the preferred embodiments of the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications, and equivalents that may be included within the spirit and scope of the invention. Furthermore, in the following detailed description of the present invention, numerous specific details are set forth in order to provide a thorough understanding of the present invention. However, it will readily be apparent to one skilled in the art that the present invention may be practiced without these specific details.

Embodiments of the present invention advantageously provide extra-protection fins and pads that prevent embarrassing and unwanted leakage of menstrual fluid and/or other vaginal discharge onto clothing and/or bedding during periods of heavy flow and/or when lying down, such as at night and/or when sleeping. Other embodiments advantageously provide methods of making and using extra-protection fins and pads. Although the invention is described with respect to menstrual fluid and/or vaginal discharge, the invention is not so limited and may be used to prevent leakage resulting from adult incontinence, hemorrhoids, surgery, and/or other genital/rectal fluid discharge or flow. The invention, in its various aspects, will be explained in greater detail below with regard to exemplary embodiments.

Exemplary Extra-Protection Fins

Figure 1:
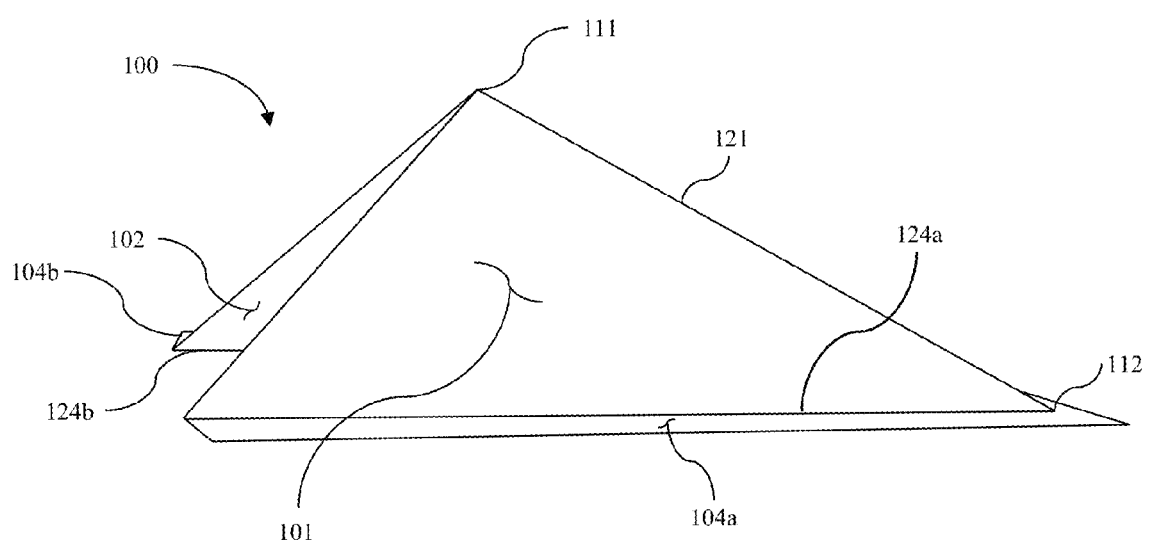
FIG. 1 is a perspective view of an extra-protection fin according to one embodiment of the present disclosure.

Referring now to FIG. 1, an exemplary extra-protection fin 100 is shown comprising (a) a first triangular face 101, (b) a second triangular face 102 foldably attached and/or connected at an angle to the first triangular face 101 at a first edge 121, (c) a top apex 111, and (d) a front apex 112. The extra-protection fin 100 is configured such that when the fin 100 is positioned with the front apex 112 at or near a woman's vagina and the top apex 111 at or near her anus, the front apex 112 initially catches the flow of menstrual fluid and/or other vaginal discharge. As the flow and/or discharge continues, the extra-protection fin fills backwards, toward the top apex 111. Each of the triangular faces, 101, 102 may also comprise a flat, horizontal band 104a, 104b foldably attached and/or connected at an angle to a corresponding base edge 124a, 124b.

In the embodiment of FIG. 1, the extra-protection fin may comprise one or more layers (e.g. 1, 2, 3, 4, etc.), and may be formed by folding, either by hand, or by use of convention folding equipment and processes. The layer(s) may comprise one or more materials (e.g., cotton, soft cotton, silk, paper, wood pulp, cellulous wood fibers, fluff pulp, etc.), which may be bleached or unbleached. In some instances portions of the fin may have cover (e.g., a woven cover, a porous and/or treated non-woven cover, etc.) to provide extra absorbency, and/or a barrier membrane (e.g., a polyethylene film, a laminated sheet, etc.) to further prevent leakage. In some embodiments, the extra-protection fin may comprise a superabsorbent polymer and/or gel (e.g., sphagnum, polyacrylate, and/or other conventional absorbent materials). The material may also comprise a disinfectant (e.g., zeolite and/or other conventional disinfectant) and/or antibacterial agent (e.g., a negative-ion strip or other conventional antibacterial).

The extra-protection fin 100 may be positioned adjacent to the body inside an undergarment and tucked near or between the lips of the vagina and/or the cheeks of the buttocks. Additionally, it may be secured to the undergarment using conventional fasteners (e.g., pins, safety pins, snaps, hook and loop fasteners, tape, double sided tape, glue and/or other adhesive, etc.). In further embodiments, the extra-protection fin may be held in place utilizing one or more belts, strings, and/or straps, and/or similar devices.

In some embodiments, the extra-protection fin 100 may comprise a malleable and/or pliable material (e.g., foam, "memory foam", viscoelastic polyurethane, shape memory polymers, cross-linked polymers, thermoplastic polymers, etc.) that may mold and/or conform to the contours of a person's body when in use and/or when heated, and may act as a "stopper," preventing the leakage of menstrual fluids, other vaginal discharge and/or urine. In such embodiments, the fin 100 may also comprise an absorbent fabric cover (e.g., cotton, soft cotton, cotton fleece, bamboo fleece, hemp fleece, hemp French terrycloth, microfiber terrycloth, etc.) surrounding the pliable material. In some instances, the absorbent fabric cover may be removable and/or disposable. In some variations, the shape of fin 100 may be molded at the time of manufacture, based on custom measurements of a person's body.

The extra-protection fin may have a length of about 25 mm to 150 mm (e.g. 25 mm, 32 mm, 50 mm, 75 mm, 130 mm, etc.). The height of the extra-protection fin 100 may range from about 0.25 mm at the front apex 112 to about 40 mm at the top apex 111 (e.g., 0.25 mm-10 mm, 0.25 mm-12 mm, 0.50 mm-20 mm, 0.50 mm-35 mm, 0.50 mm-40 mm, etc.) and any ranges therein. The width of the extra-protection fin may range from about 0.25 mm at the front apex 112 to 75 mm at the end of the fin 100 furthest from the front apex 112 (e.g., 0.25 mm-25 mm, 0.25 mm-35 mm, 0.50 mm-50 mm, 0.50 mm-60 mm, 0.50 mm-75 mm, etc.) and any ranges therein.

Figure 2A:
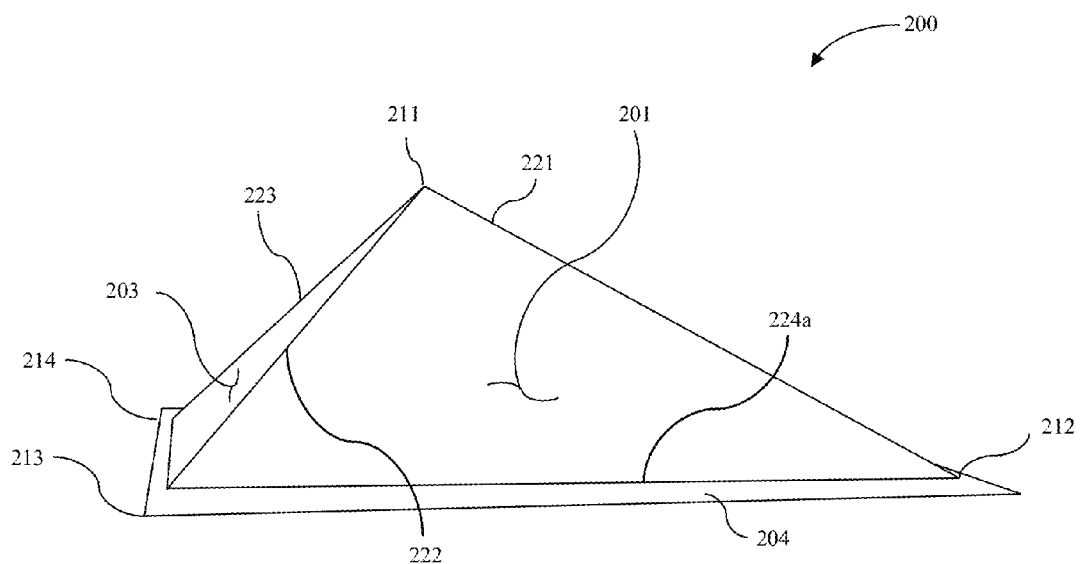
FIG. 2A is perspective view of an extra-protection fin according to a second embodiment of the present disclosure.
Figure 2B:
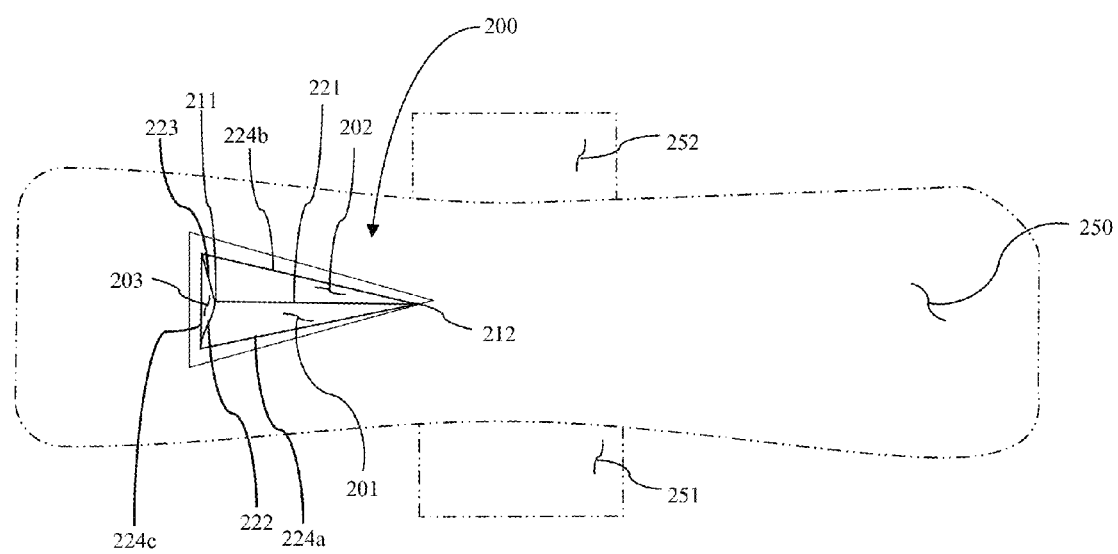
FIG. 2B is a top view of the fin of FIG. 2A, attached to a conventional menstrual pad having wings.

Referring now to FIGS. 2A-B, an exemplary extra-protection fin 200 is shown having (a) a first triangular face 201, (b) a second triangular face 202 foldably attached and/or connected to the first triangular face 201 at an edge 221, (c) a third triangular face 203, foldably attached and/or connected to the first triangular face 201 at a second edge 222 and to the second triangular face 202 at a third edge 223, (d) a top apex 211, (e) a front apex 212. The first, second and third triangular faces 201-203 meet at the top apex 211. The extra-protection fin 200 is configured such that when the fin 200 is positioned with the front apex 212 at or near a woman's vagina and the top apex 211 at or near her anus, the front apex 212 catches the flow of menstrual fluid and/or other vaginal discharge first, and as the flow and/or discharge continues, the extra-protection fin fills backwards, toward the top apex 211.

In some embodiments, the extra-protection pad may also comprise a triangular base 204, and in some such embodiments, the triangular base 204 may extend beyond base edges 224a-224c of the first, second and third faces 201-203 respectively, such that the triangular base 204 may be used for securing the extra-protection fin 200 to an undergarment.

As shown in FIG. 2B, when adhered to a conventional menstrual pad 250 having wings 251-252 for securing the pad 250 to an undergarment, the extra-protection fin 200 may be configured such that the front apex 212 is at or near the center of the pad 250 and top apex 211 may be at or near the rear of the pad 250. However, in other embodiments, the extra-protection fin may be positioned such that the front apex 212 is closer to the front of the pad. In other embodiments, the front apex may be positioned closer to the rear of the pad. Positioning the front apex closer to the rear of the pad is particularly advantageous when the pad is being used to catch and/or absorb rectal discharge (e.g., discharge from hemorrhoids). When used to catch and/or absorb vaginal discharge, the front apex 212 is located at or near a woman's vagina such that the front apex 212 absorbs the menstrual fluid and/or vaginal discharge first, and as the flow continues, the extra-protection fin 200 fills backwards away from the front apex 212 toward the top apex 211.

The extra-protection fin 200 of FIGS. 2A-B may comprise the same material(s) as described above for the extra-protection fin of FIG. 1, and may have the same ranges of length, width and height as described therein.

In some embodiments, the extra-protection fin 200 may comprise a foam or "memory foam" (e.g., viscoelastic polyurethane and/or other materials conventional foam materials) that may mold and/or conform to the contours of a body when in use. In other embodiments the extra-protection fin 200 may be contoured at the time of manufacture. In some embodiments, the base 204 may comprise an adhesive layer with a peel-off backing to adhere the extra-protection fin to a conventional menstrual pad.

Exemplary Extra-Protection Pads with Fins

Figure 3A:
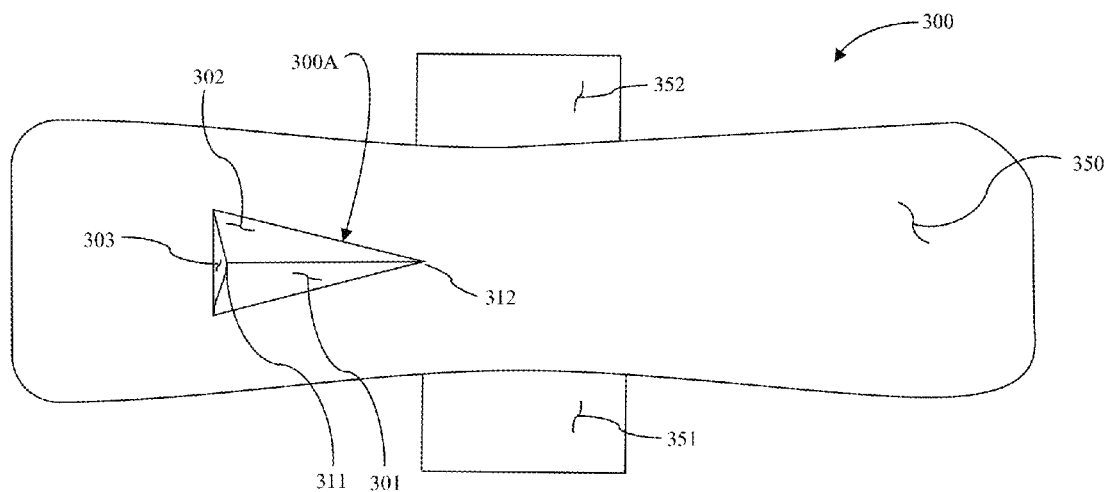
FIG. 3A is a top view of an extra-protection pad having a built-in fin and wings according to an embodiment of the present disclosure.
Figure 3B:
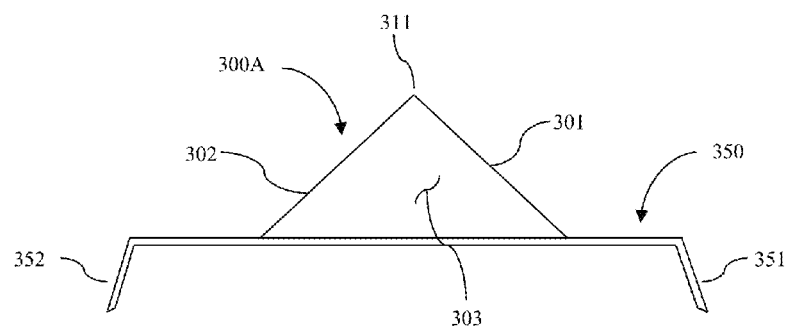
FIG. 3B is a rear view of the extra-protection pad of FIG. 3A with the wings partially folded down.
Figure 3C:
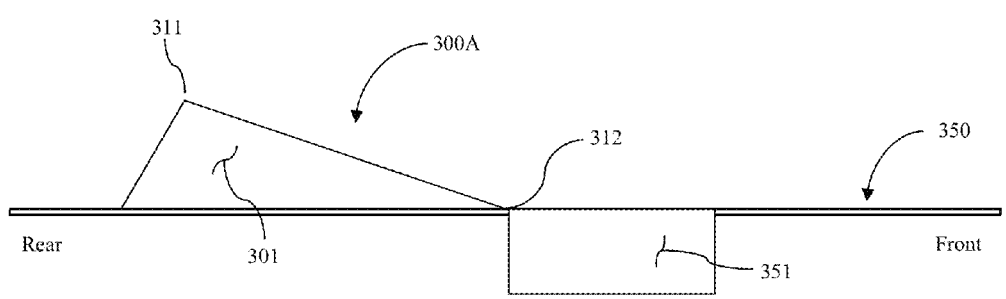
FIG. 3C is a side view of the extra-protection pad of FIG. 3A with the wings partially folded down.

Referring now to FIGS. 3A-C, therein is shown a top, a rear and a side view, respectively, of an extra-protection pad 300 comprising a menstrual pad 350 having wings 351 and 352, and an extra-protection fin 300A, which may be attached to the extra-protection pad 300 during the manufacturing process. Fin 300A comprises a first triangular face 301, a second triangular face 302 foldably attached and/or connected to the first triangular face 301 at an edge 321, a third triangular face 303 foldably attached and/or connected to the first triangular face 301 at a second edge 322 and to the second triangular face 302 at a third edge 323, a top apex 311 and a front apex 312. The extra-protection pad 300 is configured such that when the fin 300A is positioned with the front apex 312 at or near a woman's vagina and the top apex 311 at or near her anus, the front apex 312 catches the flow of menstrual fluid and/or other vaginal discharge first, and as the flow and/or discharge continues, the extra-protection fin fills backwards, toward the top apex 311. As the menstrual flow and/or other vaginal discharge continues, the fin 300A fills from the front apex 312 toward the top apex 311.

The fin 300A and menstrual pad 350 of FIGS. 3A-C may comprise the same material(s) as described above for the extra-protection fin 100 of FIG. 1 and the fin 200 of FIGS. 2A and 2B, and the fin 300A may have the same ranges of length, width and height as described therein. The menstrual pad 350 may comprise of the same materials as the fin 300A or the extra-protection fin 300A and menstrual pad 350 may comprise one or more different materials.

The fin 300A may be attached to the menstrual pad 350 during the manufacturing process by any conventional means (e.g., by gluing and/or otherwise adhering, tacking, sewing, stitching, bonding, etc.). In some instances, the fin 300A may have a horizontal band surrounding the fin 300A at its base, or it may have a triangular base that extends beyond base edges of the fin 300A (not shown; see e.g., base 204 of FIG. 2A). The horizontal band, flat surface, or triangular base may aid in the attachment of the fin 300A to the menstrual pad 350. In embodiments with a horizontal band or triangular base, the band or base may comprise one or more of the same materials as the extra-protection fin 300A and/or the pad 350 to which the fin 300A is attached.

The fin 300A may be roughly centered on the width of the menstrual pad 350 between the wings 351, 352 (see FIG. 3B) so as to align the front apex 312 and the top apex 311 with an imaginary line from the center of a woman's vagina to the center of her anus. The wings 351, 352 and/or the natural folds of the woman's body keep the extra-protection pad 300 and the fin 300A positioned so as to catch the menstrual fluid and/or other vaginal discharge.

As can be seen in FIG. 3C, the fin 300A is positioned such that the apex 311 of the fin 300 is closer to the rear (anus end) of the extra-protection pad 300. However, in some embodiments, the fin 300A may be positioned such that the apex 311 is centered on the pad 300, halfway between the front and the rear of the extra-protection pad 300. In other embodiments, the apex 311 may be positioned at or near the rear of the extra-protection pad 300. With regard to the position of the fin 300A along the width of the pad 300, the fin 300A typically will be positioned such that the apex 311 is centered between the left and ride sides of the menstrual pad 350, as shown in FIG. 3B.

Figure 4:
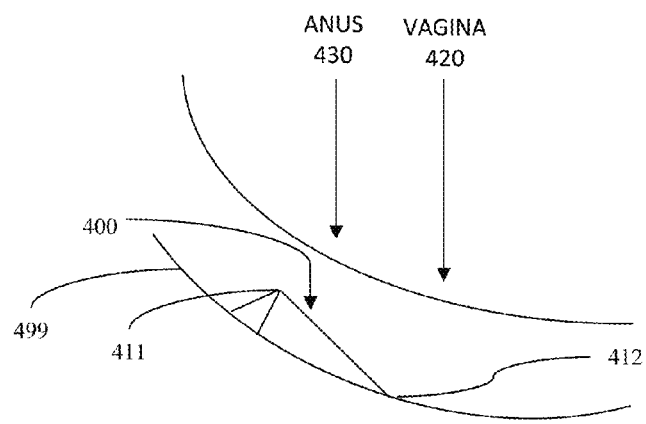
FIG. 4 is a schematic view of an extra-protection fin showing the relationship of the fin to a woman's body according to an embodiment of the present disclosure.

Referring now to FIG. 4, a schematic view of the fin 400 is shown in relationship to a woman's vagina 420, her anus 430, and her underwear 499, according to an embodiment of the present disclosure. In the embodiment of FIG. 4, the front apex 412 of fin 400 is located at or near the vagina 420 and is positioned such that the top apex 411 of fin 400 is at or near the anus 430. In some embodiments, the front apex 412 may be positioned slightly in front or slightly to the rear of the vagina 420, and the top apex 411 may be positioned at or to the rear of the anus 430. Longer fins (e.g., having a length of 75 mm or longer), the fin 400 may be positioned such that the front apex 412 is just slightly in front of the vagina, and the top apex may be at or to the rear of the anus. In one embodiment, the apex 411 may extend upward to contact the anus 430. In other embodiments the apex 411 may be positioned below the anus 430. In yet other embodiments the apex 411 may be positioned behind or to the rear of the anus 430.

Extra-Protection "Sandwich" Pads

Figure 5:
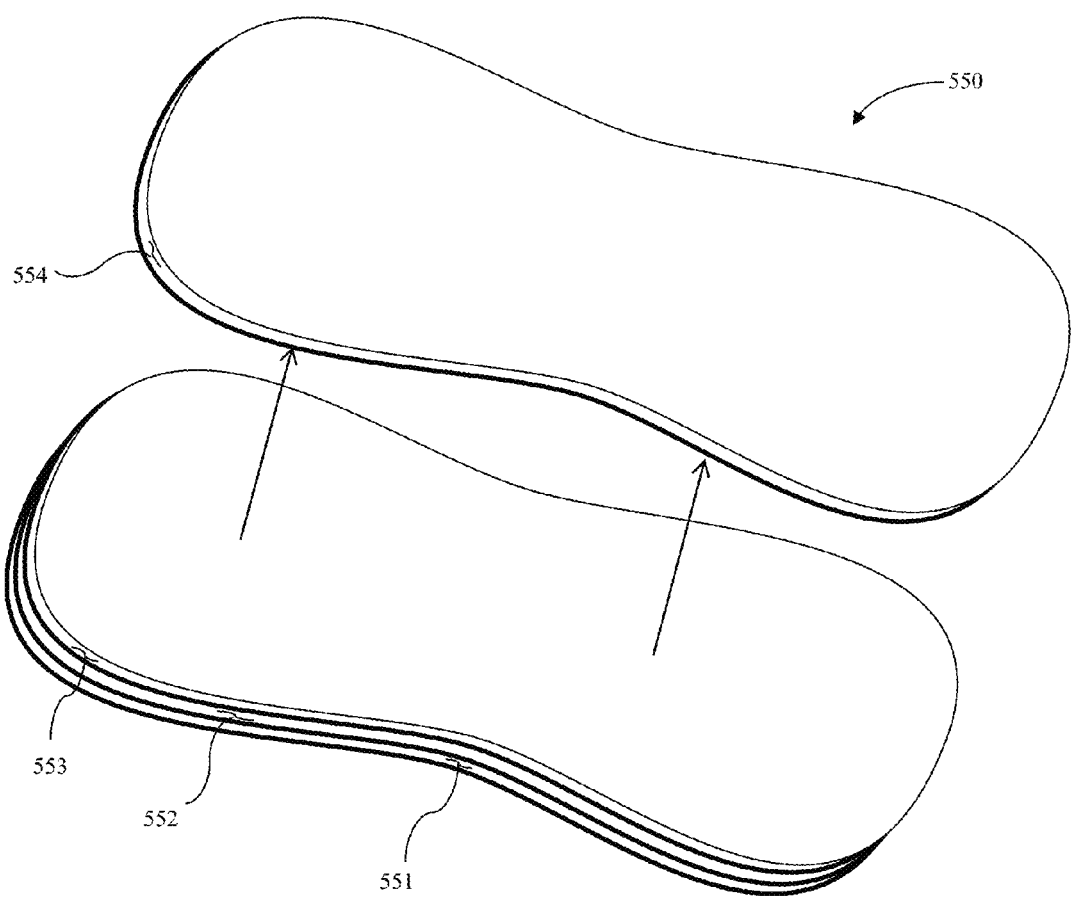
FIG. 5 is an expanded view of a "sandwiched" pad according to an embodiment of the present disclosure.

Referring now to FIG. 5, therein is shown a perspective view of an embodiment of the present disclosure wherein the extra-protection pad 550 comprises a bottom layer 551, intermediate layers 552-553 and a top layer 554, all of which are stacked and/or "sandwiched" together to form a highly absorbent extra-protection pad 550. Each of the intermediate layers 552-553 and the top layer 554 may have an adhesive (e.g., a hot-melt, thermoplastic, ethylene-vinyl acetate, epoxy, polyurethane, cyanoacrylate, etc.) applied to the underneath side of the layer so as to adhere the intermediate layers 552-553 and the top layer 554 to the adjacent layer below. Likewise, the bottom layer 551 may have an adhesive applied to the underneath side of the layer to adhere the bottom layer 551 to an undergarment (not shown).

As the menstrual fluid and/or other vaginal discharge is captured by the top layer 554 and the top layer 554 becomes soiled, the top layer 554 may be peeled away from the adjacent intermediate layer 553 below to expose a clean and sanitary layer with which to catch additional menstrual fluid and/or other vaginal discharge. Then, as the intermediate layer 553 captures fluid and/or discharge and becomes soiled, the intermediate layer 553 may also be peeled away from the next intermediate layer 552, to expose another clean and sanitary surface, and so on.

In some embodiments, the extra-protection pad 550 comprises only a top layer and a bottom layer. In other embodiments, the extra-protection pad 550 comprises from one to as many as twenty intermediate layers (e.g., 2, 3, 4, 6, 10, 13, 15, 16, etc.). In an instance of the present disclosure, the top layer 554, the bottom layer 551 and/or intermediate layers 552-553 may contain a coagulant and/or a topical hemostatic agent (not shown) to thicken the menstrual flow and/or other vaginal discharge into a soft or semi-solid mass, thereby further preventing the flow and/or discharge from leaking from the extra-protection pad 550. The coagulant and topical hemostatic agents may be conventional materials and agents (e.g., acrylates, polyacrylate gels, sphagnum, ferric subsulfate solutions, microfibrillar collagen products, chitosan dressings, etc.).

Extra-Protection Pads with Lips

Figure 6:
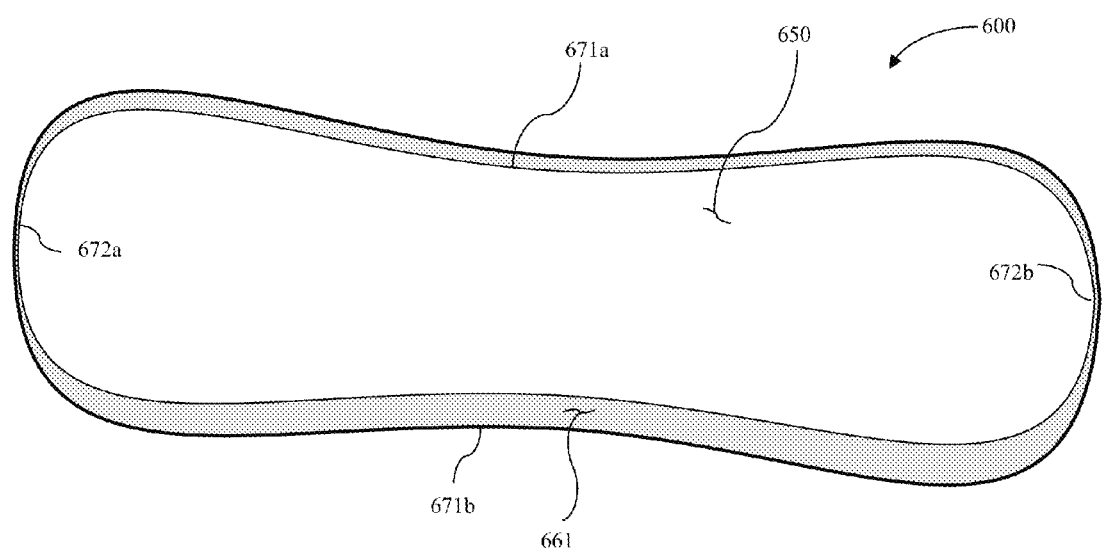
FIG. 6 is a perspective view of an extra-protection pad having a lip around the entirety of the pad according to an embodiment of the present disclosure.

Referring now to FIG. 6, an embodiment of an extra-protection pad 600 is shown comprising a menstrual pad 650 with a first pair of opposing edges 671a-b having an approximately linear and/or a slightly curved shape, and a second pair of opposing edges 672a-b, having an approximately half ovoid or half elliptical shape. The first pair of opposing edges 671a-b, and the second pair of opposing edges 672a-b together comprise the entire perimeter edge of the menstrual pad 650. The extra-protection pad 600 also comprises a lip 661 attached and/or otherwise connected to first opposing edges 671a-b and the second opposing edges 672a-b. The lip 661 is configured to act as a physical barrier to prevent leakage from the edges 671a-b and 672a-b of the menstrual pad 650.

The lip 661 may comprise the same material or materials as that of the menstrual pad 650, or in other embodiments, may comprise one or more materials different than that of the menstrual pad 650. For example, the lip 661 may comprise cotton, soft cotton, a cotton-blend, foam, "memory" foam (e.g., viscoelastic polyurethane and/or other materials conventional foam materials), a polymer, polyethylene film, and/or other porous and absorbent, or non-porous materials.

The lip 661 and the menstrual pad 650 may be formed from the same material by folding the first and second pairs of opposing edges 671a-b and 672a-b upward to form lip 661. In other embodiments the first and second pair of opposing edges may be formed by stamping, molding, roll forming and/or other conventional means. Alternately, the lip 661 may be formed from one or more different materials, and may be attached and/or connected to the first opposing edges 671a-b and/or the second opposing edges 672a-b (e.g., by sewing, stitching, bonding, gluing, adhering, etc.).

The lip 661 of FIG. 6 is shown surrounding the entire perimeter of menstrual pad 650 (i.e., lip 661 has approximately the same length as the total length of first opposing edges 671a-b and the second opposing edges 672a-b). However, in some embodiments, the lip 661 may not surround the entire perimeter of the menstrual pad 650, and instead, may be some percentage (e.g., 25%, 32%, 50%, 75%, 90%, etc.) of the total perimeter length. In other embodiments, two lips (not shown) may be positioned opposite each other on the first pair of opposing edges 671a-b and may be less than or equal to the length of the first opposing edges 671a-b. Alternatively, two lips may be positioned opposite each other on the second pair of opposing edges 672a-b and likewise may be less than or equal to the length of the second opposing edges 672a-b. In embodiments where the length of the lips is less than the length of the first or second opposing edges 671a-b or 672a-b, respectively, the lips may be centered along the length of the corresponding opposing edges 671a-b or 672a-b, and the length of the lips may be a percentage (e.g., 25%, 32%, 50%, 75%, 90%, etc.) of the length of the corresponding opposing edges 671a-b or 672a-b.

The lip 661 may have a height ranging from a 0.25 millimeters to a centimeter or more (e.g. 0.25 mm, 0.50 mm, 0.75 mm, 1 mm, 2 mm, 3 mm, 5 mm, 7 mm, 1 cm, 1.5 cm, etc.) and/or any range therein, and the height may vary along the length of the opposing edges 671a-b and/or 672a-b. For example, the height of lip 661 may range from 0.25 mm at points nearest the ends of opposing edges 671a-b, and increase in height to a maximum height of 1.5 cm or more at or near the center of opposing edges 671a-b.

In some embodiments, the lip 661 and/or the menstrual pad 650 may comprise a polyethylene film to provide a further leak-proof barrier. In some embodiments, the menstrual pad 650 may contain a coagulant and/or topical hemostatic agent. In some embodiments, the surface of the menstrual pad 650 may be treated with a disinfectant and/or an antibacterial agent. The coagulant and topical hemostatic agent may be as described with regard to FIG. 5, above. The disinfectant and antibacterial agents may comprise those materials referenced with regard to FIG. 1 above.

Figure 7:
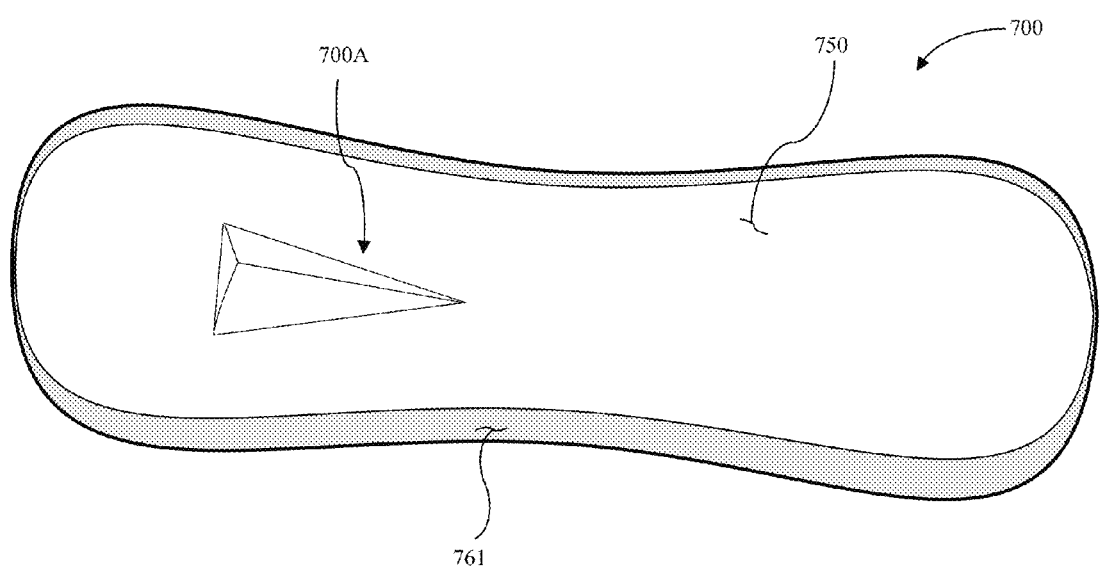
FIG. 7 is a perspective view of an extra-protection pad having a fin and a lip according to an embodiment of the present disclosure.

Although the exemplary embodiment of FIG. 6 does not contain an extra-protection fin, some embodiments of the present disclosure may comprise an extra-protection fin 700A attached to a menstrual pad 750 as shown in FIG. 7. In such instances, the menstrual pad 750 and/or extra-protection fin may comprise an ultra-thin, highly absorbent material and/or superabsorbent polymer (e.g., an acrylic polymer, polyacrylic acid, etc.). The extra-protection pad 700 may also comprise a lip 761, attached and/or otherwise connected to the menstrual pad 750 at its perimeter. The lip 761 may have a height that is the same over the entire length of the lip 761, or the lip 761 may vary in height as described above for lip 661 of FIG. 6.

Figure 8:
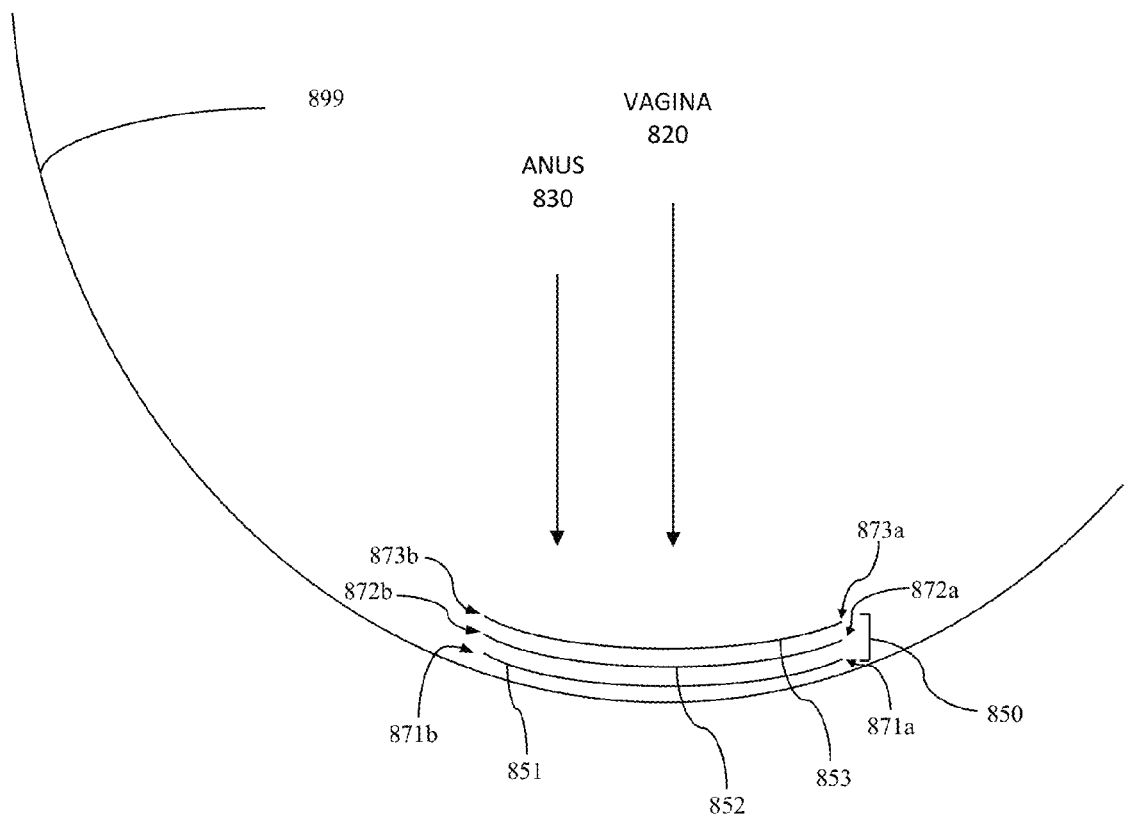
FIG. 8 is a schematic view showing multiple plies of an ultra-thin extra protection pad showing the relationship of the pad to the body according to an embodiment of the present disclosure.

Referring now to FIG. 8, therein is shown a schematic view of a multi-ply (multi-layered) extra-protection pad 850 (e.g., the multi-layered extra-protection pad 550 of FIG. 5), having plies (layers) 851-853, leading edges 871a-873a and trailing edges 871b-873b, shown in relationship to a woman's vagina 820, her anus 830, and an undergarment 899. As can be seen in FIG. 8, most typically, when the multi-ply extra-protection pad 850 is placed adjacent to the body and inside the undergarment, the leading edges 871a-873a of the plies 851-853 are positioned such that the leading edges 871a-873a are located in front of the vagina 820. Similarly, the trailing edges 871b-873b are positioned such that the trailing edges 871b-873b are located rearward of the anus 830.

Figure 9A:
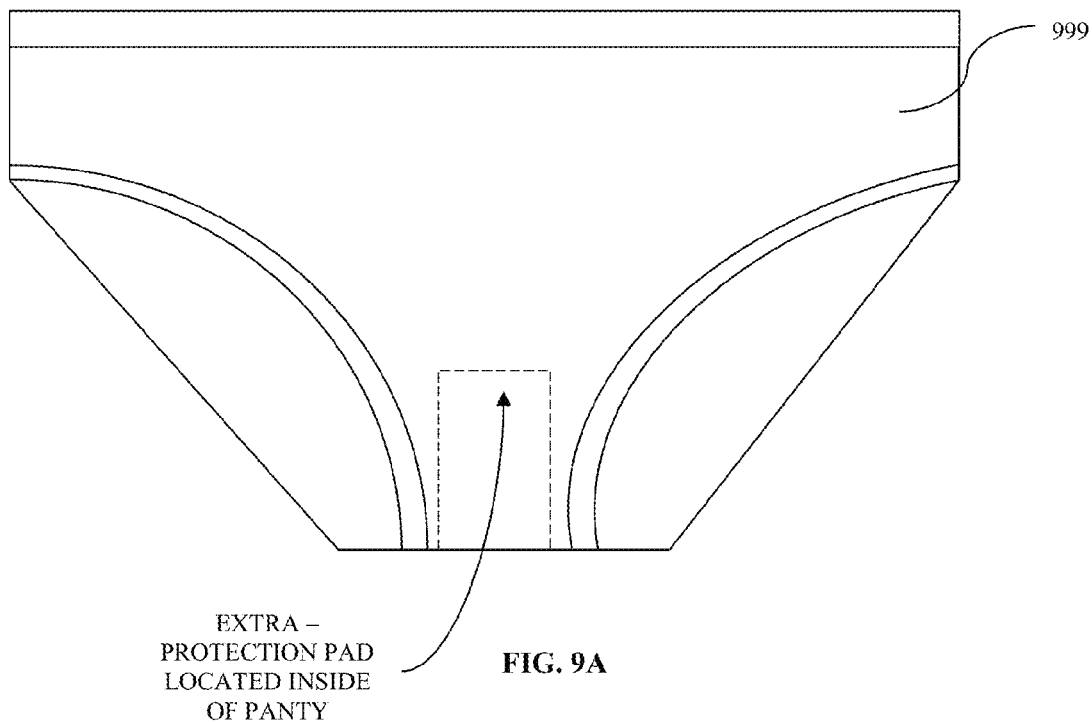
FIG. 9A is a front view showing the location of the extra-protection pad in an undergarment according to an embodiment of the present disclosure.
Figure 9B:
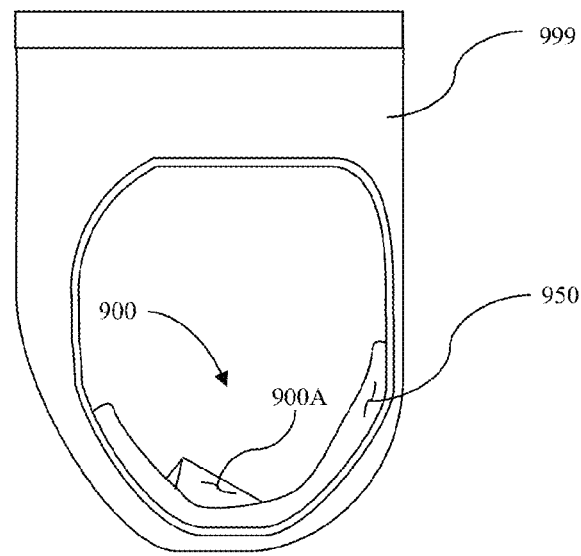
FIG. 9B is a side view of an undergarment showing the location of the extra-protection pad according to an embodiment of the present disclosure.

Referring now to FIGS. 9A and 9B, therein is shown a front view and a side view of an undergarment 999, demonstrating the most typical and approximate location of the extra-protection pad 900, comprising a menstrual pad 950 and an extra-protection fin 900A, when used to collect the flow of menstrual fluid and/or other vaginal discharge. As can be seen from FIGS. 9A and 9B, the extra-protection pad 900 is located inside the undergarment positioned such that the extra-protection pad, when in use, is located between undergarment 999 and at or below the vagina and anus (not shown).

Although the extra-protection pad 900 in FIG. 9B is shown with a fin 900A, in alternate embodiments, the extra-protection pad 900 may not have a fin 900A, and instead, may comprise a coagulant and/or a topical hemostatic agent to thicken the menstrual flow and/or other vaginal discharge into a soft or semi-solid mass, thereby further preventing the flow and/or discharge from leaking from the extra-protection pad 900. In some embodiments, the extra-protection pad 900 may comprise a "sandwich" type pad (see e.g., extra-protection pad 550 of FIG. 5), and/or a lip (see e.g., lip 661 of FIG. 6 and lip 761 of FIG. 7), as described above.

Figure 10:
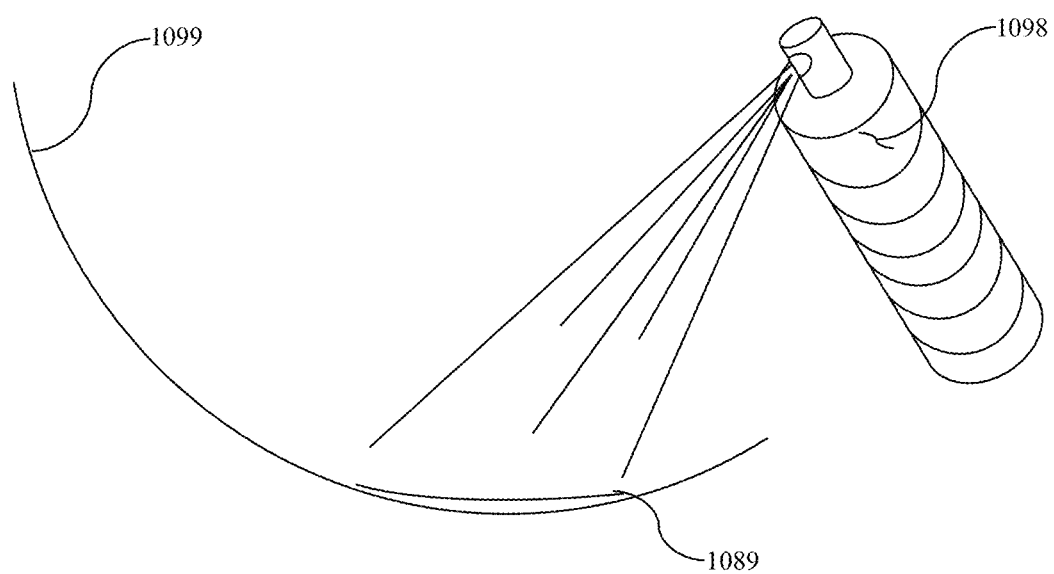
FIG. 10 is a schematic view showing the application of an ultra-absorbent coating agent being applied to an undergarment according to an embodiment of the present disclosure.

FIG. 10 shows a schematic view of a can 1098 of spray-on polymer 1089 that prevents organic compounds such as menstrual fluid and/or vaginal discharge from combining with fabric 1099, such as the fabric of undergarments and/or bed clothes. The spray polymer 1089 may be a super-absorbent polymer (e.g., anionic polyacrylamide), that is configured to be sprayed on, and then peeled off when soiled.

Exemplary Methods of Making Extra-Protection Fins and Pads

Methods of making an extra-protection fin may comprise forming a first triangular face, a second triangular face foldably attached and/or connected at an angle to the first triangular face at a first edge such that the first and the second triangular faces form a front apex and top apex, wherein the extra-protection fin is configured such that when the fin is positioned with the front apex at or near a woman's vagina discharging menstrual and/or other vaginal fluids and the top apex at or near the woman's anus, the front apex catches and/or absorbs the fluids, and the fluids fill the extra-protection fin backwards toward the top apex.

In some embodiments, the method also comprises forming a third triangular face and attaching and/or folding at an angle the third triangular face to the first triangular face to the first triangular face at a second edge and to the second triangular face at a third edge, and attaching and/or connecting the third triangular face to the first and second triangular faces at the top apex. In further embodiments, the method also comprises forming a triangular base from one or more materials, attaching the base, to the first, second and third faces, and attaching the triangular base to a menstrual pad. In some embodiments, the triangular base may extend beyond the base edges of the first, second and third triangular faces. In other embodiments, the triangular base may fit within the base edges of the first, second and third triangular faces.

The extra-protection fin may be made from a single piece of material by folding, or may be made from two or more (e.g., 2, 3, 4, 5, etc.) pieces of material by attaching and/or connecting the two or more pieces of material together (e.g., by sewing, stitching, fastening, gluing, adhering, stapling, etc.) the pieces together. In embodiments where the material is folded, the material may be folded by hand, or by machine folding, using conventional machine folding equipment. The extra-protection fin may comprise one or more materials (e.g., paper, wood pulp, cellulous wood fibers, fluff pulp, cotton, soft cotton, wool, silk, etc.). The materials may be bleached or unbleached.

In some embodiments, the method may comprise molding the extra-protection fin to the shape of the human body using conventional molding equipment and techniques. In some embodiments, the method may comprise applying an adhesive to the base, the adhesive configured to connect the extra-protection fin to a conventional menstrual pad. In embodiments where an adhesive is applied, typically the method will comprise applying a peel-off backing to the adhesive to maintain the adhesive properties until use.

In some embodiments, the method may comprise attaching the extra-protection fin to a menstrual pad by applying glue and/or another adhesive, and/or by tacking, sewing and/or stitching the fin to the pad during the manufacturing process. In some embodiments, the method may include coating, inserting and/or impregnating the extra-protection fin and/or the pad with a coagulant, a super-absorbent gel, a disinfectant and/or an antibacterial agent using conventional means.

In some embodiments an extra-protection pad may be made by applying an adhesive to the bottom of a plurality of layers and pressing the layers together, to join the layer above to the next adjacent layer below. In some embodiments, a lip may be added to the extra-protection pad by folding first and second pairs of opposing edges upward to form the lip and/or by stamping, molding and/or other conventional means.

Exemplary Methods of Using an Extra-Protection Pad

In some embodiments, the method of using an extra-protection fin of the present disclosure may comprise (i) placing the extra-protection fin on a conventional menstrual pad such that when the menstrual pad is placed next to the body, the front apex is located at or near the vagina and the top apex is located at or near the anus, (ii) and attaching the fin to the conventional pad (e.g., by pinning, stapling, gluing, adhering, stitching, sewing). In some embodiments, attaching the extra-protection fin to the conventional pad may include (a) grasping a protective strip positioned on a base of the fin, (b) peeling off from the base a protective strip to expose an adhesive, and (c) pressing the fin onto the menstrual pad.

In embodiments where the extra-protection fin is attached to a menstrual pad prior to distribution, the method of using the extra-protection pad may comprise (i) placing the extra-protection pad in an undergarment such that when the undergarment is worn, the extra-protection pad is adjacent to the body, the front apex of the extra-protection fin is located at or near the vagina, and the top apex of the fin is located at or near the anus, and (ii) wearing the undergarment.

CONCLUSION

Thus, embodiments of the present disclosure advantageously provide a disposable fin and/or pad that prevents leakage of menstrual fluid and/or other vaginal discharge during periods of heavy flow, at night, and/or when lying down, thereby avoiding embarrassment, staining of clothing and/or bedding, and the resultant increased expenses from laundering and/or premature disposal of the clothing and/or bedding. Embodiments of the present disclosure also advantageously provide methods of making and using extra-protection fins and pads.

The foregoing descriptions of specific embodiments of the present invention have been presented for purposes of illustration and description. They are not intended to be exhaustive or to limit the invention to the precise forms disclosed. Obviously, many modifications and variations are possible in light of the above teaching. The embodiments were chosen and described in order to best explain the principals of the invention and its practical application, to thereby enable others skilled in the art to best utilize the invention and the various embodiments and modifications as are suited to the particular use contemplated. It is intended that the scope of the invention be defined by the components and elements described herein and their equivalents.

What is claimed is:

1. An extra-protection fin comprising:
   (a) a first triangular face having a first fold edge and a first base edge;
   (b) a second triangular face having a second base edge, the second triangular face foldably attached and/or connected at an angle to the first triangular face at the first fold edge such that the first and second triangular faces form a front apex at a single point where the first fold edge and the first and second base edges meet, and a top apex; and
   the extra-protection fin configured such that when the fin is positioned with the front apex at or near a woman's vagina discharging menstrual and/or other vaginal fluids and the top apex at or near the woman's anus, the front apex catches and/or absorbs the fluids first, and the extra-protection fin fills backwards toward the top apex.

2. The extra-protection fin of claim 1, wherein each of the first and second triangular faces comprise a band foldably attached and/or connected at an angle to, respectively, the first and second base edges and wherein each band is approximately the same length as its respective first or second base edge and, wherein the bands are configured to secure the extra-protection fin to an undergarment.

3. The extra-protection fin of claim 1, further comprising a third triangular face having a third base edge, the third triangular face foldably attached and/or connected at an angle to the first triangular face at a second fold edge and to the second triangular face at a third fold edge, and wherein a vertex of the third triangular face contacts and/or is connected to the first and second triangular faces at the top apex.

4. The extra-protection fin of claim 3, wherein the first, second and third triangular faces are contoured to a woman's body shape.

5. The extra-protection fin of claim 3, wherein the first, second and third triangular faces comprise two or more layers.

6. The extra-protection fin of claim 3, wherein the first, second and third triangular faces comprise memory foam, viscoelastic polyurethane, shape memory polymers, cross-linked polymers and/or thermoplastic polymers that conform to the contours of a women's body shape when in use and/or when heated.

7. The extra-protection fin of claim 3, further comprising a triangular base, wherein the triangular base is attached and/or connected to the first, second and third triangular faces at the first, second and third base edges and wherein the triangular base extends beyond the base edges of the first, second and third triangular faces and is configured to secure the extra-protection fin to an undergarment.

8. The extra-protection-fin of claim 7, wherein the fin is attached and/or connected to a menstrual pad.

9. The extra-protection pad of claim 8, further comprising wings, an adhesive and/or peel and stick strips configured to attach the extra-protection pad to an undergarment.

10. The extra-protection fin of claim 3, wherein the first, second and third triangular faces comprise cotton, soft cotton, silk, paper, wood pulp, chemical pulp, cellulous wood fibers, foam, memory foam, viscoelastic polyurethane, non-woven fabric, air-laid paper, and/or fluff pulp.

11. The extra-protection fin of claim 3, wherein the first, second and third triangular faces comprise a superabsorbent polymer, a disinfectant and/or an antibacterial agent.

12. An extra-protection pad comprising:
(a) a bottom layer;
(b) a plurality of intermediate layers;
(c) a top layer; and
(d) an extra-protection fin, the extra-protection fin comprising:
  (i) a first triangular face having a first fold edge and a first base edge;
  (ii) a second triangular face having a second base edge, the second triangular face foldably attached and/or connected at an angle to the first triangular face at the first fold edge such that the first and second triangular faces form a front apex at a single point where the first fold edge and the first and second base edges meet, and a top apex;
  (iii) a third triangular face foldably attached and/or connected at an angle to the first triangular face at a second fold edge and to the second triangular face at a third fold edge such that a vertex of the third triangular face contacts and/or connects to the first and second triangular faces at the top apex, and
the extra-protection fin configured such that when the fin is positioned with the front apex at or near a woman's vagina discharging menstrual and/or other vaginal fluids and the top apex at or near the woman's anus, the front apex catches and/or absorbs the fluids first, and the extra-protection fin fills backwards toward the top apex; and
the extra-protection pad configured such that the bottom layer, the plurality of intermediate layers, and the top layer are stacked and/or sandwiched together, and
the top layer and each of the intermediate layers comprise an adhesive applied to an underneath side of the layer configured to adhere the top layer and each of the intermediate layers to an adjacent layer below such that, when soiled and/or saturated, the layer(s) may be peeled away and/or removed from an adjacent clean and/or sanitary layer below.

13. The extra-protection pad of claim 12, wherein each of the bottom, intermediate and top layers has a lip at or near perimeter edges of the pad that extends upward at a height above a surface of the respective layer.

14. The extra-protection pad of claim 12, wherein the bottom, intermediate and/or top layer(s) comprise a coagulant and/or topical hemostatic agent.

15. The extra-protection pad of claim 14, wherein the coagulant and/or topical hemostatic agent comprises acrylates, polyacrylate gels, sphagnum, ferric subsulfate solutions, microfibrillar collagen products, and/or chitosan dressings.

16. The extra-protection pad of claim 12, wherein the first, second and third triangular faces comprise memory foam and/or heat-sensitive thermoplastic polymers that mold and/or conform to a woman's body.

17. A method of making an extra-protection fin, the method comprising:
(a) forming a first triangular face and a second triangular face;
(b) attaching and/or folding at an angle the first triangular face to the second triangular face at a first fold edge such that the first and second triangular faces form a front apex at a single point where the first fold edge and the first and second base edges meet, and a top apex;
the extra-protection fin configured such that when the fin is positioned with the front apex at or near a woman's vagina discharging menstrual and/or other vaginal fluids and the top apex at or near the woman's anus, the front apex catches and/or absorbs the fluids first, and the extra-protection fin fills backwards toward the top apex.

18. The method of claim 17, also comprising:
(c) forming a third triangular face;
(d) attaching and/or folding at an angle the third triangular face to the first triangular face at a second fold edge and to the second triangular face at a third fold edge, wherein a vertex of the third triangular face contacts and/or is connected to the first and second triangular faces at the top apex.

19. The method of claim 18, wherein the method also comprises (e) attaching a triangular base to the first, second and third triangular faces at the first, second and third base edges, and wherein the base extends beyond base edges of the first, second and third triangular faces, and (f) attaching the base to a menstrual pad.

20. The method of claim 19, wherein the method also comprises forming the first, second and third triangular faces and/or the triangular base from two or more layers of material.

21. The method of claim 19, further comprising forming a lip at or near edges of the menstrual pad, wherein the lip extends upward at a height above a surface of the pad.

* * * * *